US006242649B1

(12) United States Patent
Beckhaus et al.

(10) Patent No.: US 6,242,649 B1
(45) Date of Patent: Jun. 5, 2001

(54) CONTINUOUS METHOD FOR PRODUCING AROMATIC AMINES

(75) Inventors: Heiko Beckhaus, Leverkusen; Reinhard Langer, Tönisvorst, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/529,143

(22) PCT Filed: Oct. 2, 1998

(86) PCT No.: PCT/EP98/06275

§ 371 Date: Apr. 7, 2000

§ 102(e) Date: Apr. 7, 2000

(87) PCT Pub. No.: WO99/19292

PCT Pub. Date: Apr. 22, 1999

(51) Int. Cl.⁷ .................................................. C07C 209/00
(52) U.S. Cl. ........................ 564/422; 564/416; 564/420; 564/423
(58) Field of Search .................................... 564/422, 416, 564/420, 423

(56) References Cited

U.S. PATENT DOCUMENTS

| 5,563,296 | * | 10/1996 | Zarnack et al. | 564/422 |
| 5,779,995 |   | 7/1998  | Witt et al.    | 422/215 |

FOREIGN PATENT DOCUMENTS

| 2106644 |   | 8/1972 | (DE) . |
| 2135154 |   | 2/1973 | (DE) . |
| 9720804 | * | 6/1997 | (WO) . |

* cited by examiner

Primary Examiner—Samuel Barts
(74) Attorney, Agent, or Firm—Joseph C. Gil; Lyndanne M. Whalen

(57) ABSTRACT

A continuous process for the preparation of aromatic di- and/or polyamines by catalytic hydrogenation of the corresponding aromatic di- and/or polynitro compounds with hydrogen, characterized in that, in a reactor with a catalytic fixed bed or trickle bed at a pressure between 5 and 100 bar and a reaction temperature of from 100 to 220° C.

a) the aromatic di- and/or polynitro compounds, optionally in the presence of a solvent, are introduced into a product stream comprising essentially recycled hydrogenated product, water and hydrogen, and b) a part of the product stream is removed continuously from the reactor system.

13 Claims, 2 Drawing Sheets

CONTINUOUS METHOD FOR PRODUCING AROMATIC AMINES

A continuous process for the preparation of aromatic amines The invention relates to a continuous process for the preparation of aromatic di- and polyamines by catalytic hydrogenation of the di- and polynitro compounds corresponding to the amines at high temperatures and optionally with simultaneous removal of heat from the reaction mixture in order to generate steam with a pressure above atmospheric of >1.5 bar abs. on a fixed bed.

Processes for the preparation of aromatic amines by catalytic hydrogenation of the nitro compounds on which they are based are known in large number (DE-A-2 135 155, DE-A-2 106 644, DE-A-4 435 839, EP-A-0 696 573 and WO 97/20 804).

Generally speaking, the industrial-scale catalytic hydrogenation of aromatic polynitro compounds in suspensions is carried out at low temperatures because there is a risk of uncontrolled secondary reactions during the hydrogenation of aromatic polynitro compounds at high temperatures. These secondary reactions may lead to the formation of unwanted by-products and hence to reductions in yield. Reactions involving hydrogenation of the nucleus, hydrogenolytic cleavage or the formation of high molecular weight, tar-like products may be mentioned by way of example in this connection. Explosive secondary reactions may also take place which are due to the highly exothermic course of the nitro group reaction and its high rate of reaction at relatively high temperatures.

When aromatic polynitro compounds are reacted with hydrogen, a considerable amount of heat is released. Advantageous hydrogenation processes are those in which the increased reaction energy does not have to be destroyed with an expenditure of energy but in which the reaction energy can be utilised economically in the form of steam production.

Fouling and deposits of catalysts are observed time and again in the catalytic suspension processes. Product impurities, relatively poor hydrogenation yields and high catalyst consumptions are often associated with this. The expenditure on cleaning and maintenance is considerable.

Thelen et al. (DE-A-2 135 154 and DE-A-2 135 155) have circumvented these disadvantages by the description of catalytic hydrogenation on a fixed bed. In spite of the advantageous arrangement of the catalyst in a fixed bed, the disadvantages are that the quantity of heat is removed in the reactor, the dimensions and structure of the reactor and the deposition of the catalyst in spinel form onto the cooling tubes are very expensive. The throughput of aromatic polynitro compounds is small. The removal of heat is problematic and the reaction must be carried out only at low temperatures.

The catalytic hydrogenation of aromatic nitro compounds on a fixed bed in a combination of two fixed bed reactors is described in WO 97/20 804 (Chambost et al.). The division of the product quantities after the first reactor with simultaneous gas separation is problematic and expensive. Disadvantages of the process described here are the use of two reactors and the low reaction temperatures of up to 120° C. Moreover, large quantities of solvents such as alcohols or ethers are used in some cases, the solvent having to be separated from the aromatic diamine after the reaction and optionally worked up.

Figure 1:
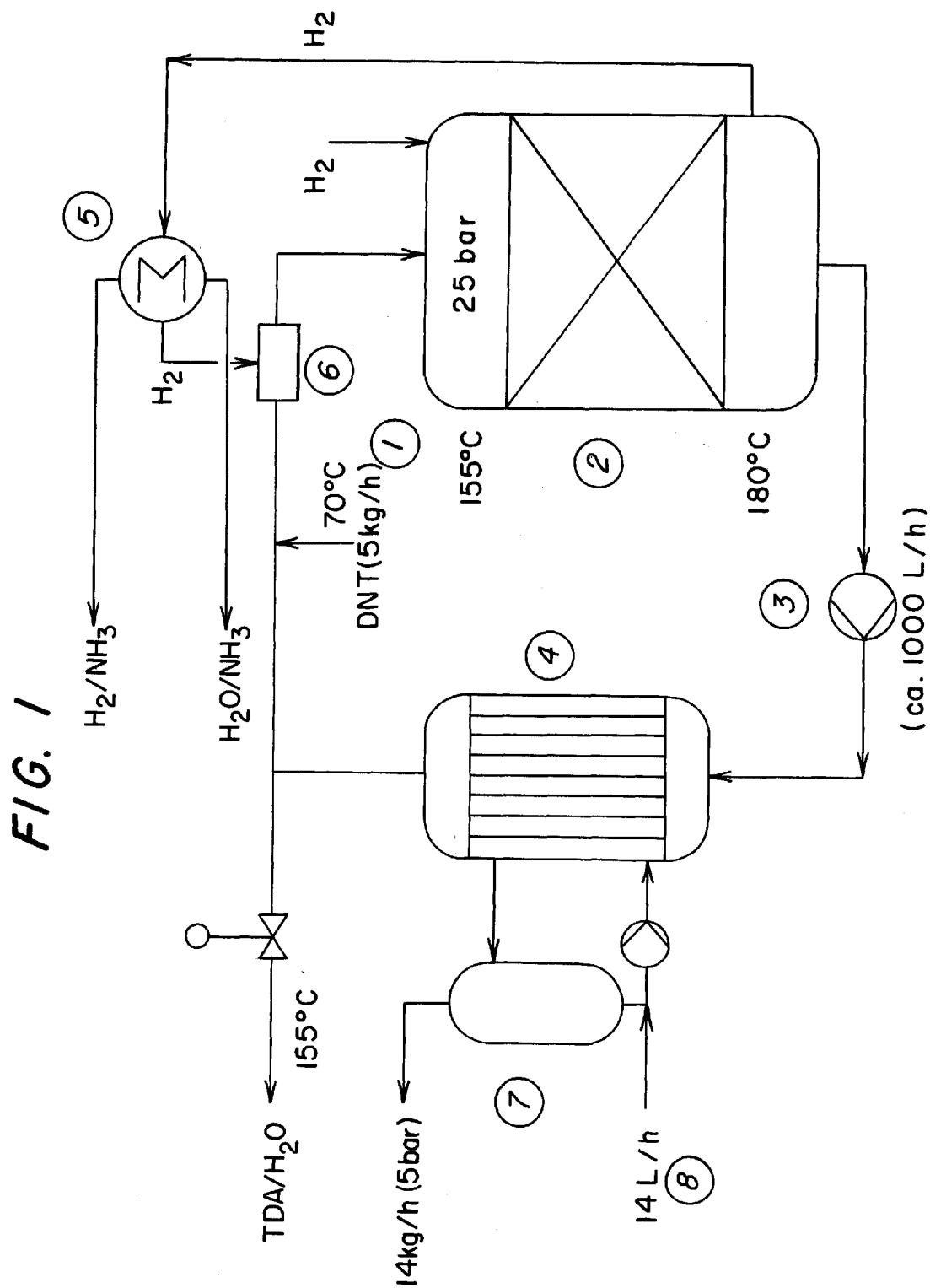
FIG. 1 illustrates apparatus having a trickle bed catalyst which is suitable for carrying out the process of the present invention.

The object was, therefore, to provide an improved process for the preparation of amines by hydrogenation of aromatic nitro compounds which makes it possible to operate without solvents or only with little solvent even at high temperatures without secondary reactions or fouling occurring.

The invention relates to a continuous process for the preparation of aromatic di- and/or polyamines by catalytic hydrogenation of the corresponding aromatic di- and/or polynitro compounds with hydrogen, in which, in a reactor with a catalytic fixed bed or trickle bed at a pressure between 5 and 100 bar and a reaction temperature from 100 to 220° C., a) the aromatic di- and/or polynitro compounds, optionally in the presence of a solvent, are introduced into a product stream comprising essentially recycled hydrogenated product, water and hydrogen, and b) a part of the product stream is removed continuously from the reactor system.

A pressure of 10 to 80 bar and an operating temperature of 150 to 200° C. are preferably maintained in the reactor.

The reactor used preferably has an external heat exchanger so that the heat of reaction produced can be used for steam generation.

The product discharge may take place at any place in the reactor system. The discharge takes place preferably after the external heat exchanger before pumping. The product stream removed from the reaction system is advantageously cooled to about 150 to 160° C.

Examples of aromatic nitro compounds used in preference are:

1,3-dinitrobenzene, 2,4-dinitrotoluene, 2,6-dinitrotoluene or industrial dinitrotoluene mixtures composed essentially of the last two isomers mentioned.

Aromatic nitro compounds used in particular preference are 2,4-dinitrotoluene or industrial mixtures thereof with up to 35 wt. %, based on the total mixture, of 2,6-dinitrotoluene. These industrial mixtures may also contain secondary quantities, i.e. up to a maximum of 6 wt. %, based on the total mixture, of 2,3-,2,5- or 3,4-dinitrotoluene.

The inherently known hydrogenation catalysts for nitro compounds are used for the process according to the invention. The catalysts, shaken in the solid form, adhering to supports, grids, packings or fabrics, may be arranged geometrically as required in such a way that the pressure drop is as low as possible, the distribution over the catalyst bed is optimal, and the speed of the reaction mixture is high enough to absorb the heat of reaction. Highly suitable catalysts are, in particular, made of metals of the 8th subsidiary group of the periodic system of elements, which are used, for example, on support materials such as oxides of magnesium, aluminium titanium and/or nickel, including Raney-Nickel. Nickel catalysts are used in preference. Noble metal catalysts on a suitable support material such as, e.g., palladium on carbon, may also be used. The catalysts are preferably in the pressed solid form, dumped on textured bases.

The process according to the invention is carried out preferably in such a way that the circulation of the reaction mixture over a fixed bed or trickle bed is operated in such a way that the volumetric ratio of the mixture to the nitro compound introduced is 50 to 500, preferably 200 to 300, the hydrogen feed is a self-suction feed, i.e. the hydrogen gas collecting in the upper part of the reactor is mixed of its own accord back into the reaction mixture by the energy of the circulated mixture, the operating pressure of the reactor system is maintained by feeding in fresh hydrogen from outside, the volumetric ratio of the incoming hydrogen stream to the pumped mixture is 0.1 to 7, the hydrogen required being withdrawn from the gas chamber of the reactor and the hydrogen consumed during the reaction being replenished in any part of the system, the ratio of catalyst to nitro compound introduced is <20 kg/kgh and preferably 5 to 14 kg/kgh.

Due to the mixing of the aromatic nitro component with the recycled hydrogenated product (product loop), intensive mixing and distribution over the catalyst bed is obtained with the other process parameters. As a result, catalytic hydrogenation, optionally also solvent-free, of di- or polyaromatics is possible at high temperatures, so that steam at a pressure above atmospheric of more than 2 bar may be generated at the same time by removing heat from the system. Secondary reactions or the like occur only to a minor extent, if at all.

In order to regenerate the catalyst bed, the metered addition of the aromatic di- and/or polynitro compounds is interrupted, if necessary. In a simple manner, the catalyst may thus be regenerated by means of the product stream which continues to flow without a lengthy interruption of the process being required for said regeneration.

Optionally, the aromatic di- and/or polynitro compounds may be metered into the product stream preferably also in a solvent. Suitable solvents are aliphatic $C_1$ to $C_4$ alcohols, particularly methanol, ethanol, isopropanol, t-butanol or cyclic ethers, particularly dioxane or tetrahydrofuran.

Figure 2:
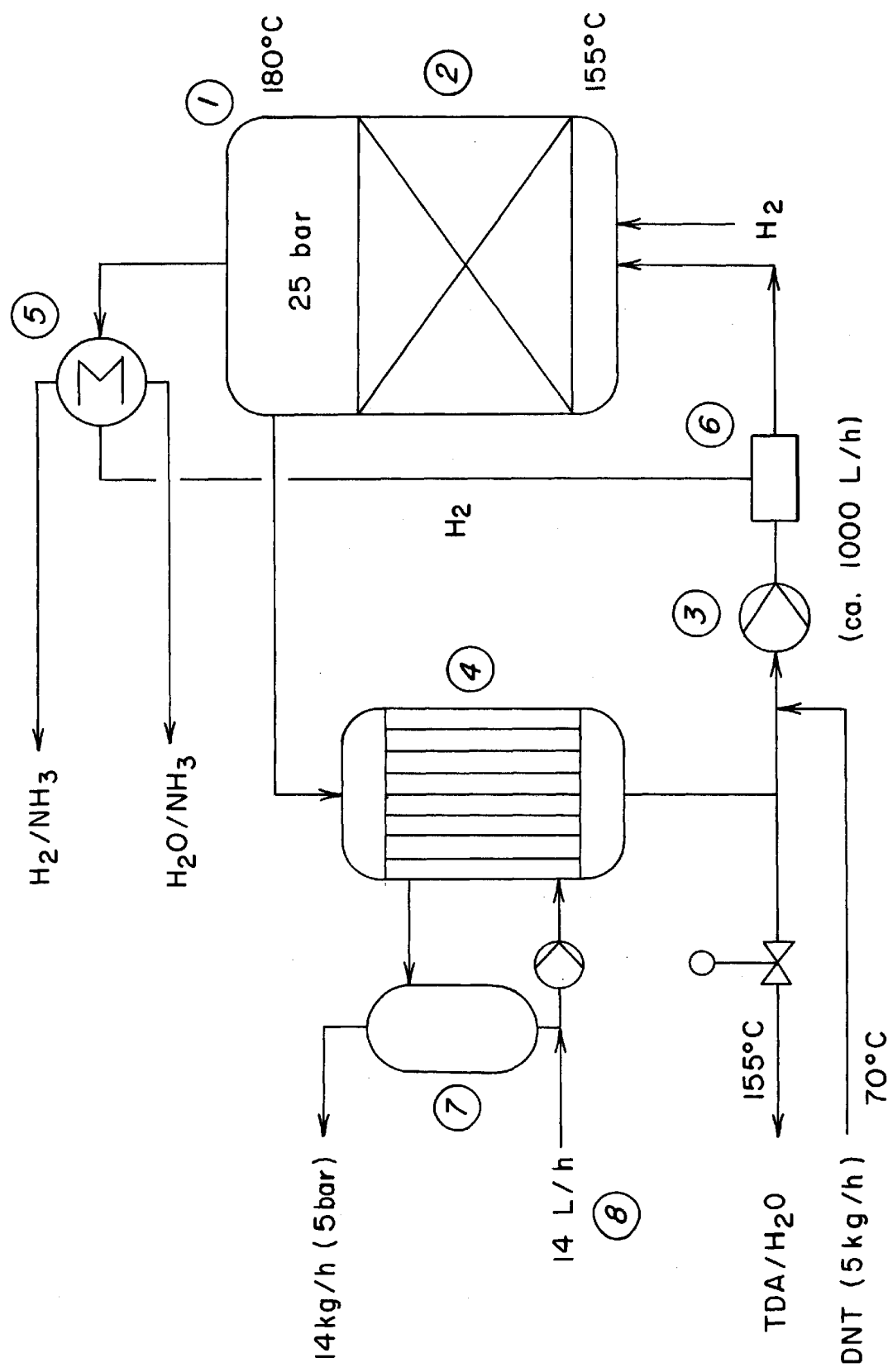
FIG. 2 illustrates an apparatus having a fixed bed catalyst which is suitable for carrying out the process of the present invention.

The process according to the invention may be carried out e.g. in a reaction system which is represented schematically in FIG. 1 (trickle bed) or alternatively in FIG. 2 (fixed bed). The numbers in these Figures have the following meaning:
1) Reactor
2) Catalyst bed
3) Pipe systems. Pump for recycling the reaction mixture
4) Heat exchanger for cooling the circulated reaction mixture
5) Gas cooler
6) Intake of circulating hydrogen
7) Steam separator
8) Condensate The invention will be explained in more detail on the basis of the examples below without limiting its scope.

EXAMPLES

EXAMPLE 1
(Compare FIG. 1)

In an autoclave 1 (diameter 14 cm) with a trickle bed (catalyst 50 ml Ra-Nickel, pressed, cubic mouldings: 3 to 4 mm in diameter, 5 to 6 mm in height), 1,000 l/h of T DA/water mixture are pumped 3 from above via a heat exchanger 4. The hydrogen-containing, cooled gas 5 is pumped out of the reactor via an injector 4 by means of the liquid stream cooled from 180° C. to 155° C. 5 kg/h of dinitrotoluene (70° C.), liquid, are added before the hydrogen circulation. The hydrogen consumed by the reaction is added from above by fresh hydrogen in co-current. In accordance with the metered addition of the nitro compound, the TDA isomers and water of reaction are obtained stoichiometrically, selectively, in a >99% yield.

EXAMPLE 2
(Compare FIG. 2)

In an autoclave 1 (diameter 14 cm) with a fixed bed (catalyst 50 ml as in Example 1), 1,000 l/h of TDA/water mixture are pumped from below via a heat exchanger 2. Hydrogen-containing, cooled gas 5 is pumped out of the reactor via an injector 4 by means of the liquid stream cooled from 180° C. to 155° C. 5 kg/h of dinitrotoluene (70° C.), liquid, are added before the pump 3. The hydrogen consumed by the reaction is added from below by fresh hydrogen in co-current. In accordance with the metered addition of the nitro compound, the TDA isomers and water of reaction are obtained stoichiometrically, selectively, in a >99.2% yield.

What is claimed is:

1. A continuous process for the production of aromatic diamines and/or polyamines comprising
    a) introducing an aromatic dinitro compound and/or polynitro compound into a product stream comprising recycled hydrogenated product, water and hydrogen,
    b) reacting the aromatic dinitro compound and/or polynitro compound with hydrogen in a reactor having a fixed bed catalyst or a trickle bed catalyst at a temperature of from about 100 to about 220° C. and a pressure between 5 and 100 bar,
    c) removing heat generated during step b) through an external loop which includes a heat exchanger, and
    d) continuously removing a portion of the product of b).

2. The process of claim 1 in which the aromatic dinitro compound and/or polynitro compound is a mixture of (1) a dinitro compound and/or polynitro compound and (2) the corresponding diamine or polyamine and water.

3. The process of claim 1 in which an aromatic dinitro compound is used.

4. The process of claim 3 in which the aromatic dinitro compound is 2,4-dinitrotoluene or a mixture of 2,4-dinitrotoluene and 2,6-dinitrotoluene.

5. The process of claim 1 in which the volumetric ratio of the product stream comprising recycled hydrogenated product, water and hydrogen to the aromatic dinitro compound and/or polynitro compound introduced into that product stream is from about 50 to about 500.

6. The process of claim 1 in which the ratio of catalyst to aromatic dinitro compound and/or polynitro compound is less than 20 kg/kgh.

7. The process of claim 1 in which the ratio of catalyst to aromatic dinitro compound and/or polynitro compound is from about 5 to about 14 kg/kgh.

8. The process of claim 1 in which the catalyst bed is impinged from above the recycled hydrogenated product.

9. The process of claim 1 in which the catalyst bed is impinged from below the recycled hydrogenated product.

10. The process of claim 1 in which a solvent in combination with the aromatic dinitro compound and/or polynitro compound is introduced into the product stream in step a).

11. The process of claim 10 in which the solvent is selected from aliphatic $C_1$–$C_4$ alcohols and cyclic ethers.

12. The process of claim 10 in which the solvent is used in a quantity of from about 0.1 to about 40% by weight, based on the weight of the reaction mixture.

13. The process of claim 10 in which the solvent is used in a quantity of from about 1 to about 10% by weight, based on the weight of the reaction mixture.

* * * * *